(12) United States Patent
Beri

(10) Patent No.: US 7,173,122 B2
(45) Date of Patent: Feb. 6, 2007

(54) ANTISENSE OLIGONUCLEOTIDES TO TYPE I PROCOLLAGEN

(75) Inventor: Rajinder Beri, Loughborough (GB)

(73) Assignee: Rahul Kumar Nath, Houston, TX (US)

( * ) Notice: Subject to any disclaimer, the term of this patent is extended or adjusted under 35 U.S.C. 154(b) by 482 days.

(21) Appl. No.: 10/149,352

(22) PCT Filed: Dec. 12, 2000

(86) PCT No.: PCT/GB00/04741

§ 371 (c)(1),
(2), (4) Date: Jun. 10, 2002

(87) PCT Pub. No.: WO01/44455

PCT Pub. Date: Jun. 21, 2001

(65) Prior Publication Data

US 2003/0105050 A1 Jun. 5, 2003

(30) Foreign Application Priority Data

Dec. 15, 1999 (GB) .................................. 9929487.8

(51) Int. Cl.
*C07H 21/04* (2006.01)
*C12Q 1/68* (2006.01)
*C12P 19/34* (2006.01)

(52) U.S. Cl. ................... 536/24.5; 536/23.1; 435/6; 435/91.1

(58) Field of Classification Search .................... None
See application file for complete search history.

(56) References Cited

U.S. PATENT DOCUMENTS

| | | | | |
|---|---|---|---|---|
| 5,874,553 A | * | 2/1999 | Peyman et al. | 536/22.1 |
| 6,007,995 A | * | 12/1999 | Baker et al. | 435/6 |
| 6,127,346 A | * | 10/2000 | Peyman et al. | 514/44 |
| 6,265,157 B1 | * | 7/2001 | Prockop et al. | 435/6 |
| 2004/0005663 A1 | * | 1/2004 | Bell et al. | 435/69.1 |

FOREIGN PATENT DOCUMENTS

| EP | 736608 A1 | * | 10/1996 |
|---|---|---|---|
| WO | WO 93/11149 | | 6/1993 |
| WO | WO 94/11494 | | 5/1994 |
| WO | WO 94/22487 | | 10/1994 |
| WO | WO 98/33904 | | 8/1998 |
| WO | WO 99/49065 | | 9/1999 |

OTHER PUBLICATIONS

Opalinska et al. Nucleic acid therapeutics: Basic principles and recent applications. Nature Review, 2002, vol. 1, pp. 503-514.*

Crooke, S.T. Progress in antisense technology 2004 Annu. Rev. Med. vol. 55, pp. 61-95.*

Jen et al. Supression of gene expression by targeted disruption of messenger RNA: Available options and current strategies 2000 Stem Cells vol. 18: pp. 307-319.*

Agrawal et al. Antisense therapeutics: is it as simple as complementary base recognition? 2000 Mol. Med. Tod. vol. 6: pp. 72-81.*

Altmann, K.H. et al., "Novel Chemistry", pp. 73-107, 1998., XP-002119324.

Ausserlechner, MJ et al.., "Altered Procollagen mRNA Expression during the Progression of Avian Scleroderma", *Molecular Medicine*, vol. 3, No. 10, pp. 654-662, 1997., XP-000986380.

Colige, A. et al., "Use of Antisense Oligonucleotide To Inhibit Expression of a Mutated Human Procollagen Gene (COL1A10 in Transfected Mouse 3T3 Cels", *Biochemistry*, vol. 32, No. 1, pp. 7-11, 1993., XP-000652779.

Hawkins, JR. et. al., "A 9-Base Pair Deletion in COL1A1 in a Lethal Variant of Osteogenesis Imperfecta", *The Journal of Biological Chemistry*, vol. 266, No. 33, pp. 22370-22374, 1991., XP-000942166.

Khillan, JS. et al., "Partial Rescue of a Lethal Phenotype of Fragile Bones in Transgenic Mice with a Chimeric Antisense Gene Directed Against a Mutated Collagen Gene", *Proc. Natl. Acad. Sci. USA.*, vol. 91, pp. 6298-6302, 1994., XP-000942172.

Laptev, AV. Et. al., Specific Inhibition of Expression of a Human Collagen Gene (COL1A1) with Modified Antisense Oligonucleotides. The Most Effective Target Sites Are Clustered in Double-Stranded Regions of the Predicted Secondary Structure for the mRNA, *Biochemistry*, vol. 33, pp. 1033-11039, XP-000984496, 1994., XP-000984496.

Onoda, K. et. al., "Role of Extracellular Matrix in Experimental Vasospasm: Inhibitory Effect of Antisense Oligonucleotide on Collagen Induction", *Stroke*, vol. 37, No. 11, pp. 2102-2108, 1994., XP-000984053, 1996.

Prockop, DJ. et. al., "Mutations in Type 1 Procollagen That Cause Osteogenesis Imperfecta: Effects of the Mutations on the Assembly of Collagen into Fibrils, the Basis of Phenotypic Variations, and Potential Antisense Therapies", *Journal of Bone and Mineral Research*, vol. 8, Sapp.. 2, pp. S489-S492, 1993., XP-000674592.

Ririe, SS. and Guntaka, RV., "An RNA Oligonucleotide Corresponding to the Polypyrimidine Region of the Rat α 1 (1) Procollagen Promoter Forms a Stable Triplex and Inhibits Transcription", *Biochemical and Biophysical Research Communications*, vol. 249, pp. 218-221, 1998., XP-000942267.

Uhlmann, E. and Peyman, A., "Antisense Oligonucleotides: A New Therapeutic Principle", *Chemical Reviews*, vol. 90, No. 4, pp. 543-584, 1990., XP-000141412.

* cited by examiner

*Primary Examiner*—James Schultz
*Assistant Examiner*—Tracy Vivlemore
(74) *Attorney, Agent, or Firm*—The Matthews Firm

(57) ABSTRACT

The invention provides antisense DNA oligonucleotides which are effective in inhibiting the expression of a wild type COL1A1 gene.

2 Claims, No Drawings

SEQUENCE LISTING

```
<160> NUMBER OF SEQ ID NOS: 14
<210> SEQ ID NO 1
<211> LENGTH: 6728
<212> TYPE: DNA
<213> ORGANISM: Homo sapiens
<220> FEATURE:
<221> NAME/KEY: CDS
<222> LOCATION: (120)..(4511)
<220> FEATURE:
<221> NAME/KEY: sig_peptide
<222> LOCATION: (120)..(185)

<400> SEQUENCE: 1
agcagacggg agtttctcct cggggtcgga gcaggaggca cgcggagtgt gaggccacgc      60
atgagcggac gctaaccccc tccccagcca caaagagtct acatgtctag ggtctagac      119 atg ttc agc ttt gtg gac ctc cgg ctc ctg ctc ctc tta gcg gcc acc      167
Met Phe Ser Phe Val Asp Leu Arg Leu Leu Leu Leu Leu Ala Ala Thr
  1               5                  10                  15 gcc ctc ctg acg cac ggc caa gag gaa ggc caa gtc gag ggc caa gac      215
Ala Leu Leu Thr His Gly Gln Glu Glu Gly Gln Val Glu Gly Gln Asp
             20                  25                  30 gaa gac atc cca cca atc acc tgc gta cag aac ggc ctc agg tac cat      263
Glu Asp Ile Pro Pro Ile Thr Cys Val Gln Asn Gly Leu Arg Tyr His
         35                  40                  45 gac cga gac gtg tgg aaa ccc gag ccc tgc cgg atc tgc gtc tgc gac      311
Asp Arg Asp Val Trp Lys Pro Glu Pro Cys Arg Ile Cys Val Cys Asp
     50                  55                  60 aac ggc aag gtg ttg tgc gat gac gtg atc tgt gac gag acc aag aac      359
Asn Gly Lys Val Leu Cys Asp Asp Val Ile Cys Asp Glu Thr Lys Asn
 65                  70                  75                  80
```

```
tgc ccc ggc gcc gaa gtc ccc gag ggc gag tgc tgt ccc gtc tgc ccc         407
Cys Pro Gly Ala Glu Val Pro Glu Gly Glu Cys Cys Pro Val Cys Pro
                85                  90                  95 gac ggc tca gag tca ccc acc gac caa gaa acc acc ggc gtc gag gga         455
Asp Gly Ser Glu Ser Pro Thr Asp Gln Glu Thr Thr Gly Val Glu Gly
            100                 105                 110 ccc aag gga gac act ggc ccc cga ggc cca agg gga ccc gca ggc ccc         503
Pro Lys Gly Asp Thr Gly Pro Arg Gly Pro Arg Gly Pro Ala Gly Pro
        115                 120                 125 cct ggc cga gat ggc atc cct gga cag cct gga ctt ccc gga ccc ccc         551
Pro Gly Arg Asp Gly Ile Pro Gly Gln Pro Gly Leu Pro Gly Pro Pro
    130                 135                 140 gga ccc ccc gga cct ccc gga ccc cct ggc ctc gga gga aac ttt gct         599
Gly Pro Pro Gly Pro Pro Gly Pro Pro Gly Leu Gly Gly Asn Phe Ala
145                 150                 155                 160 ccc cag ctg tct tat ggc tat gat gag aaa tca acc gga gga att tcc         647
Pro Gln Leu Ser Tyr Gly Tyr Asp Glu Lys Ser Thr Gly Gly Ile Ser
                165                 170                 175 gtg cct ggc ccc atg ggt ccc tct ggt cct cgt ggt ctc cct ggc ccc         695
Val Pro Gly Pro Met Gly Pro Ser Gly Pro Arg Gly Leu Pro Gly Pro
            180                 185                 190 cct ggt gca cct ggt ccc caa ggc ttc caa ggt ccc cct ggt gag cct         743
Pro Gly Ala Pro Gly Pro Gln Gly Phe Gln Gly Pro Pro Gly Glu Pro
        195                 200                 205 ggc gag cct gga gct tca ggt ccc atg ggt ccc cga ggt ccc cca ggt         791
Gly Glu Pro Gly Ala Ser Gly Pro Met Gly Pro Arg Gly Pro Pro Gly
    210                 215                 220 ccc cct gga aag aat gga gat gat ggg gaa gct gga aaa cct ggt cgt         839
Pro Pro Gly Lys Asn Gly Asp Asp Gly Glu Ala Gly Lys Pro Gly Arg
225                 230                 235                 240 cct ggt gag cgt ggg cct cct ggg cct cag ggt gct cga gga ttg ccc         887
Pro Gly Glu Arg Gly Pro Pro Gly Pro Gln Gly Ala Arg Gly Leu Pro
                245                 250                 255 gga aca gct ggc ctc cct gga atg aag gga cac aga ggt ttc agt ggt         935
Gly Thr Ala Gly Leu Pro Gly Met Lys Gly His Arg Gly Phe Ser Gly
            260                 265                 270 ttg gat ggt gcc aag gga gat gct ggt cct gct ggt cct aag ggt gag         983
Leu Asp Gly Ala Lys Gly Asp Ala Gly Pro Ala Gly Pro Lys Gly Glu
        275                 280                 285 cct ggc agc cct ggt gaa aat gga gct cct ggt cag atg ggc ccc cgt        1031
Pro Gly Ser Pro Gly Glu Asn Gly Ala Pro Gly Gln Met Gly Pro Arg
    290                 295                 300 ggc ctg cct ggt gag aga ggt cgc cct gga gcc cct ggc cct gct ggt        1079
Gly Leu Pro Gly Glu Arg Gly Arg Pro Gly Ala Pro Gly Pro Ala Gly
305                 310                 315                 320 gct cgt gga aat gat ggt gct act ggt gct gcc ggg ccc cct ggt ccc        1127
Ala Arg Gly Asn Asp Gly Ala Thr Gly Ala Ala Gly Pro Pro Gly Pro
                325                 330                 335 acc ggc ccc gct ggt cct cct ggc ttc cct ggt gct gtt ggt gct aag        1175
Thr Gly Pro Ala Gly Pro Pro Gly Phe Pro Gly Ala Val Gly Ala Lys
            340                 345                 350 ggt gaa gct ggt ccc caa ggg ccc cga ggc tct gaa ggt ccc cag ggt        1223
Gly Glu Ala Gly Pro Gln Gly Pro Arg Gly Ser Glu Gly Pro Gln Gly
        355                 360                 365 gtg cgt ggt gag cct ggc ccc cct ggc cct gct ggt gct gct ggc cct        1271
Val Arg Gly Glu Pro Gly Pro Pro Gly Pro Ala Gly Ala Ala Gly Pro
370                 375                 380 gct gga aac cct ggt gct gat gga cag cct ggt gct aaa ggt gcc aat        1319
Ala Gly Asn Pro Gly Ala Asp Gly Gln Pro Gly Ala Lys Gly Ala Asn
```

-continued

|  |  |
|---|---:|
| 385 390 395 400 | |
| ggt gct cct ggt att gct ggt gct cct ggc ttc cct ggt gcc cga ggc<br>Gly Ala Pro Gly Ile Ala Gly Ala Pro Gly Phe Pro Gly Ala Arg Gly<br>                      405                        410                      415 | 1367 |
| ccc tct gga ccc cag ggc ccc ggc ggc cct cct ggt ccc aag ggt aac<br>Pro Ser Gly Pro Gln Gly Pro Gly Gly Pro Pro Gly Pro Lys Gly Asn<br>            420                      425                      430 | 1415 |
| agc ggt gaa cct ggt gct cct ggc agc aaa gga gac act ggt gct aag<br>Ser Gly Glu Pro Gly Ala Pro Gly Ser Lys Gly Asp Thr Gly Ala Lys<br>        435                      440                      445 | 1463 |
| gga gag cct ggc cct gtt ggt gtt caa gga ccc cct ggc cct gct gga<br>Gly Glu Pro Gly Pro Val Gly Val Gln Gly Pro Pro Gly Pro Ala Gly<br>450                      455                      460 | 1511 |
| gag gaa gga aag cga gga gct cga ggt gaa ccc gga ccc act ggc ctg<br>Glu Glu Gly Lys Arg Gly Ala Arg Gly Glu Pro Gly Pro Thr Gly Leu<br>465                      470                      475                      480 | 1559 |
| ccc gga ccc cct ggc gag cgt ggt gga cct ggt agc cgt ggt ttc cct<br>Pro Gly Pro Pro Gly Glu Arg Gly Gly Pro Gly Ser Arg Gly Phe Pro<br>                  485                      490                      495 | 1607 |
| ggc gca gat ggt gtt gct ggt ccc aag ggt ccc gct ggt gaa cgt ggt<br>Gly Ala Asp Gly Val Ala Gly Pro Lys Gly Pro Ala Gly Glu Arg Gly<br>            500                      505                      510 | 1655 |
| tct cct ggc ccc gct ggc ccc aaa gga tct cct ggt gaa gct ggt cgt<br>Ser Pro Gly Pro Ala Gly Pro Lys Gly Ser Pro Gly Glu Ala Gly Arg<br>        515                      520                      525 | 1703 |
| ccc ggt gaa gct ggt ctg cct ggt gcc aag ggt ctg act gga agc cct<br>Pro Gly Glu Ala Gly Leu Pro Gly Ala Lys Gly Leu Thr Gly Ser Pro<br>530                      535                      540 | 1751 |
| ggc agc cct ggt cct gat ggc aaa act ggc ccc cct ggt ccc gcc ggt<br>Gly Ser Pro Gly Pro Asp Gly Lys Thr Gly Pro Pro Gly Pro Ala Gly<br>545                      550                      555                      560 | 1799 |
| caa gat ggt cgc ccc gga ccc cca ggc cca cct ggt gcc cgt ggt cag<br>Gln Asp Gly Arg Pro Gly Pro Pro Gly Pro Pro Gly Ala Arg Gly Gln<br>                  565                      570                      575 | 1847 |
| gct ggt gtg atg gga ttc cct gga cct aaa ggt gct gct gga gag ccc<br>Ala Gly Val Met Gly Phe Pro Gly Pro Lys Gly Ala Ala Gly Glu Pro<br>            580                      585                      590 | 1895 |
| ggc aag gct gga gag cga ggt gtt ccc gga ccc cct ggc gct gtc ggt<br>Gly Lys Ala Gly Glu Arg Gly Val Pro Gly Pro Pro Gly Ala Val Gly<br>        595                      600                      605 | 1943 |
| cct gct ggc aaa gat gga gag gct gga gct cag gga ccc cct ggc cct<br>Pro Ala Gly Lys Asp Gly Glu Ala Gly Ala Gln Gly Pro Pro Gly Pro<br>610                      615                      620 | 1991 |
| gct ggt ccc gct ggc gag aga ggt gaa caa ggc cct gct ggc tcc ccc<br>Ala Gly Pro Ala Gly Glu Arg Gly Glu Gln Gly Pro Ala Gly Ser Pro<br>625                      630                      635                      640 | 2039 |
| gga ttc cag ggt ctc cct ggt cct gct ggt cct cca ggt gaa gca ggc<br>Gly Phe Gln Gly Leu Pro Gly Pro Ala Gly Pro Pro Gly Glu Ala Gly<br>                  645                      650                      655 | 2087 |
| aaa cct ggt gaa cag ggt gtt cct gga gac ctt ggc gcc cct ggc ccc<br>Lys Pro Gly Glu Gln Gly Val Pro Gly Asp Leu Gly Ala Pro Gly Pro<br>            660                      665                      670 | 2135 |
| tct gga gca aga ggc gag aga ggt ttc cct ggc gag cgt ggt gtg caa<br>Ser Gly Ala Arg Gly Glu Arg Gly Phe Pro Gly Glu Arg Gly Val Gln<br>        675                      680                      685 | 2183 |
| ggt ccc cct ggt cct gct gga ccc cga ggg gcc aac ggt gct ccc ggc<br>Gly Pro Pro Gly Pro Ala Gly Pro Arg Gly Ala Asn Gly Ala Pro Gly<br>690                      695                      700 | 2231 |
| aac gat ggt gct aag ggt gat gct ggt gcc cct gga gct ccc ggt agc | 2279 |

```
                                                  -continued

Asn Asp Gly Ala Lys Gly Asp Ala Gly Ala Pro Gly Ala Pro Gly Ser
705             710                 715                 720 cag ggc gcc cct ggc ctt cag gga atg cct ggt gaa cgt ggt gca gct      2327
Gln Gly Ala Pro Gly Leu Gln Gly Met Pro Gly Glu Arg Gly Ala Ala
                725                 730                 735 ggt ctt cca ggg cct aag ggt gac aga ggt gat gct ggt ccc aaa ggt      2375
Gly Leu Pro Gly Pro Lys Gly Asp Arg Gly Asp Ala Gly Pro Lys Gly
                740                 745                 750 gct gat ggc tct cct ggc aaa gat ggc gtc cgt ggt ctg acc ggc ccc      2423
Ala Asp Gly Ser Pro Gly Lys Asp Gly Val Arg Gly Leu Thr Gly Pro
                755                 760                 765 att ggt cct cct ggc cct gct ggt gcc cct ggt gac aag ggt gaa agt      2471
Ile Gly Pro Pro Gly Pro Ala Gly Ala Pro Gly Asp Lys Gly Glu Ser
770                 775                 780 ggt ccc agc ggc cct gct ggt ccc act gga gct cgt ggt gcc ccc gga      2519
Gly Pro Ser Gly Pro Ala Gly Pro Thr Gly Ala Arg Gly Ala Pro Gly
785                 790                 795                 800 gac cgt ggt gag cct ggt ccc ccc ggc cct gct ggc ttt gct ggc ccc      2567
Asp Arg Gly Glu Pro Gly Pro Pro Gly Pro Ala Gly Phe Ala Gly Pro
                805                 810                 815 cct ggt gct gac ggc caa cct ggt gct aaa ggc gaa cct ggt gat gct      2615
Pro Gly Ala Asp Gly Gln Pro Gly Ala Lys Gly Glu Pro Gly Asp Ala
                820                 825                 830 ggt gcc aaa ggc gat gct ggt ccc cct ggg cct gcc gga ccc gct gga      2663
Gly Ala Lys Gly Asp Ala Gly Pro Pro Gly Pro Ala Gly Pro Ala Gly
                835                 840                 845 ccc cct ggc ccc att ggt aat gtt ggt gct cct gga gcc aaa ggt gct      2711
Pro Pro Gly Pro Ile Gly Asn Val Gly Ala Pro Gly Ala Lys Gly Ala
850                 855                 860 cgc ggc agc gct ggt ccc cct ggt gct act ggt ttc cct ggt gct gct      2759
Arg Gly Ser Ala Gly Pro Pro Gly Ala Thr Gly Phe Pro Gly Ala Ala
865                 870                 875                 880 ggc cga gtc ggt cct cct ggc ccc tct gga aat gct gga ccc cct ggc      2807
Gly Arg Val Gly Pro Pro Gly Pro Ser Gly Asn Ala Gly Pro Pro Gly
                885                 890                 895 cct cct ggt cct gct ggc aaa gaa ggc ggc aaa ggt ccc cgt ggt gag      2855
Pro Pro Gly Pro Ala Gly Lys Glu Gly Gly Lys Gly Pro Arg Gly Glu
                900                 905                 910 act ggc cct gct gga cgt cct ggt gaa gtt ggt ccc cct ggt ccc cct      2903
Thr Gly Pro Ala Gly Arg Pro Gly Glu Val Gly Pro Pro Gly Pro Pro
                915                 920                 925 ggc cct gct ggc gag aaa gga tcc cct ggt gct gat ggt cct gct ggt      2951
Gly Pro Ala Gly Glu Lys Gly Ser Pro Gly Ala Asp Gly Pro Ala Gly
930                 935                 940 gct cct ggt act ccc ggg cct caa ggt att gct gga cag cgt ggt gtg      2999
Ala Pro Gly Thr Pro Gly Pro Gln Gly Ile Ala Gly Gln Arg Gly Val
945                 950                 955                 960 gtc ggc ctg cct ggt cag aga gga gag aga ggc ttc cct ggt ctt cct      3047
Val Gly Leu Pro Gly Gln Arg Gly Glu Arg Gly Phe Pro Gly Leu Pro
                965                 970                 975 ggc ccc tct ggt gaa cct ggc aaa caa ggt ccc tct gga gca agt ggt      3095
Gly Pro Ser Gly Glu Pro Gly Lys Gln Gly Pro Ser Gly Ala Ser Gly
                980                 985                 990 gaa cgt ggt ccc ccc ggt ccc atg ggc ccc cct gga ttg gct gga ccc      3143
Glu Arg Gly Pro Pro Gly Pro Met Gly Pro Pro Gly Leu Ala Gly Pro
                995                 1000                1005 cct ggt gaa tct gga cgt gag ggg gct cct gct gcc gaa ggt tcc cct      3191
Pro Gly Glu Ser Gly Arg Glu Gly Ala Pro Ala Ala Glu Gly Ser Pro
1010                1015                1020
```

-continued

| | |
|---|---|
| gga cga gac ggt tct cct ggc gcc aag ggt gac cgt ggt gag acc ggc<br>Gly Arg Asp Gly Ser Pro Gly Ala Lys Gly Asp Arg Gly Glu Thr Gly<br>1025                      1030                      1035                      1040 | 3239 |
| ccc gct gga ccc cct ggt gct cct ggt gct cct ggt gcc cct ggc ccc<br>Pro Ala Gly Pro Pro Gly Ala Pro Gly Ala Pro Gly Ala Pro Gly Pro<br>                   1045                      1050                      1055 | 3287 |
| gtt ggc cct gct ggc aag agt ggt gat cgt ggt gag act ggt cct gct<br>Val Gly Pro Ala Gly Lys Ser Gly Asp Arg Gly Glu Thr Gly Pro Ala<br>                  1060                      1065                      1070 | 3335 |
| ggt ccc gcc ggt ccc gtc ggc ccc gtc ggc gcc cgt ggc ccc gcc gga<br>Gly Pro Ala Gly Pro Val Gly Pro Val Gly Ala Arg Gly Pro Ala Gly<br>                1075                      1080                      1085 | 3383 |
| ccc caa ggc ccc cgt ggt gac aag ggt gag aca ggc gaa cag ggc gac<br>Pro Gln Gly Pro Arg Gly Asp Lys Gly Glu Thr Gly Glu Gln Gly Asp<br>1090                      1095                      1100 | 3431 |
| aga ggc ata aag ggt cac cgt ggc ttc tct ggc ctc cag ggt ccc cct<br>Arg Gly Ile Lys Gly His Arg Gly Phe Ser Gly Leu Gln Gly Pro Pro<br>1105                      1110                      1115                      1120 | 3479 |
| ggc cct cct ggc tct cct ggt gaa caa ggt ccc tct gga gcc tct ggt<br>Gly Pro Pro Gly Ser Pro Gly Glu Gln Gly Pro Ser Gly Ala Ser Gly<br>                  1125                      1130                      1135 | 3527 |
| cct gct ggt ccc cga ggt ccc cct ggc tct gct ggt gct cct ggc aaa<br>Pro Ala Gly Pro Arg Gly Pro Pro Gly Ser Ala Gly Ala Pro Gly Lys<br>                  1140                      1145                      1150 | 3575 |
| gat gga ctc aac ggt ctc cct ggc ccc att ggg ccc cct ggt cct cgc<br>Asp Gly Leu Asn Gly Leu Pro Gly Pro Ile Gly Pro Pro Gly Pro Arg<br>                  1155                      1160                      1165 | 3623 |
| ggt cgc act ggt gat gct ggt cct gtt ggt ccc ccc ggc cct cct gga<br>Gly Arg Thr Gly Asp Ala Gly Pro Val Gly Pro Pro Gly Pro Pro Gly<br>                  1170                      1175                      1180 | 3671 |
| cct cct ggt ccc cct ggt cct ccc agc gct ggt ttc gac ttc agc ttc<br>Pro Pro Gly Pro Pro Gly Pro Pro Ser Ala Gly Phe Asp Phe Ser Phe<br>1185                      1190                      1195                      1200 | 3719 |
| ctg ccc cag cca cct caa gag aag gct cac gat ggt ggc cgc tac tac<br>Leu Pro Gln Pro Pro Gln Glu Lys Ala His Asp Gly Gly Arg Tyr Tyr<br>                  1205                      1210                      1215 | 3767 |
| cgg gct gat gat gcc aat gtg gtt cgt gac cgt gac ctc gag gtg gac<br>Arg Ala Asp Asp Ala Asn Val Val Arg Asp Arg Asp Leu Glu Val Asp<br>                  1220                      1225                      1230 | 3815 |
| acc acc ctc aag agc ctg agc cag cag atc gag aac atc cgg agc cca<br>Thr Thr Leu Lys Ser Leu Ser Gln Gln Ile Glu Asn Ile Arg Ser Pro<br>                  1235                      1240                      1245 | 3863 |
| gag gga agc cgc aag aac ccc gcc cgc acc tgc cgt gac ctc aag atg<br>Glu Gly Ser Arg Lys Asn Pro Ala Arg Thr Cys Arg Asp Leu Lys Met<br>                  1250                      1255                      1260 | 3911 |
| tgc cac tct gac tgg aag agt gga gag tac tgg att gac ccc aac caa<br>Cys His Ser Asp Trp Lys Ser Gly Glu Tyr Trp Ile Asp Pro Asn Gln<br>1265                      1270                      1275                      1280 | 3959 |
| ggc tgc aac ctg gat gcc atc aaa gtc ttc tgc aac atg gag act ggt<br>Gly Cys Asn Leu Asp Ala Ile Lys Val Phe Cys Asn Met Glu Thr Gly<br>                  1285                      1290                      1295 | 4007 |
| gag acc tgc gtg tac ccc act cag ccc agt gtg gcc cag aag aac tgg<br>Glu Thr Cys Val Tyr Pro Thr Gln Pro Ser Val Ala Gln Lys Asn Trp<br>                  1300                      1305                      1310 | 4055 |
| tac atc agc aag aac ccc aag gac aag agg cat gtc tgg ttc ggc gag<br>Tyr Ile Ser Lys Asn Pro Lys Asp Lys Arg His Val Trp Phe Gly Glu<br>                  1315                      1320                      1325 | 4103 |
| agc atg acc gat gga ttc cag ttc gag tat ggc ggc cag ggc tcc gac<br>Ser Met Thr Asp Gly Phe Gln Phe Glu Tyr Gly Gly Gln Gly Ser Asp<br>                  1330                      1335                      1340 | 4151 |

|  |  |
|---|---|
| cct gcc gat gtg gcc atc cag ctg acc ttc ctg cgc ctg atg tcc acc<br>Pro Ala Asp Val Ala Ile Gln Leu Thr Phe Leu Arg Leu Met Ser Thr<br>1345                        1350                    1355                    1360 | 4199 |
| gag gcc tcc cag aac atc acc tac cac tgc aag aac agc gtg gcc tac<br>Glu Ala Ser Gln Asn Ile Thr Tyr His Cys Lys Asn Ser Val Ala Tyr<br>             1365                    1370                    1375 | 4247 |
| atg gac cag cag act ggc aac ctc aag aag gcc ctg ctc ctc aag ggc<br>Met Asp Gln Gln Thr Gly Asn Leu Lys Lys Ala Leu Leu Leu Lys Gly<br>1380                        1385                    1390 | 4295 |
| tcc aac gag atc gag atc cgc gcc gag ggc aac agc cgc ttc acc tac<br>Ser Asn Glu Ile Glu Ile Arg Ala Glu Gly Asn Ser Arg Phe Thr Tyr<br>             1395                    1400                    1405 | 4343 |
| agc gtc act gtc gat ggc tgc acg agt cac acc gga gcc tgg ggc aag<br>Ser Val Thr Val Asp Gly Cys Thr Ser His Thr Gly Ala Trp Gly Lys<br>1410                        1415                    1420 | 4391 |
| aca gtg att gaa tac aaa acc acc aag tcc tcc cgc ctg ccc atc atc<br>Thr Val Ile Glu Tyr Lys Thr Thr Lys Ser Ser Arg Leu Pro Ile Ile<br>1425                        1430                    1435                    1440 | 4439 |
| gat gtg gcc ccc ttg gac gtt ggt gcc cca gac cag gaa ttc ggc ttc<br>Asp Val Ala Pro Leu Asp Val Gly Ala Pro Asp Gln Glu Phe Gly Phe<br>                         1445                    1450                    1455 | 4487 |
| gac gtt ggc cct gtc tgc ttc ctg taaactccct ccatcccaac ctggctccct<br>Asp Val Gly Pro Val Cys Phe Leu<br>             1460 | 4541 |
| cccacccaac caactttccc cccaacccgg aaacagacaa gcaacccaaa ctgaaccccc | 4601 |
| ccaaaagcca aaaaatggga gacaatttca catggacttt ggaaaatatt tttttccttt | 4661 |
| gcattcatct ctcaaactta gttttatct ttgaccaacc gaacatgacc aaaaaccaaa | 4721 |
| agtgcattca accttaccaa aaaaaaaaaa aaaaaaaaa gaataaataa ataagttttt | 4781 |
| aaaaaaggaa gcttggtcca cttgcttgaa gacccatgcg ggggtaagtc cctttctgcc | 4841 |
| cgttgggtta tgaaacccca atgctgccct ttctgctcct ttctccacac ccccttggc | 4901 |
| ctcccctcca ctccttccca aatctgtctc cccagaagac acaggaaaca atgtattgtc | 4961 |
| tgcccagcaa tcaaaggcaa tgctcaaaca cccaagtggc ccccaccctc agcccgctcc | 5021 |
| tgcccgccca gcacccccag gccctgggga cctggggttc tcagactgcc aaagaagcct | 5081 |
| tgccatctgg cgctcccatg gctccttgcaa catctcccct tcgttttga gggggtcatg | 5141 |
| ccgggggagc caccagcccc tcactggggtt cggaggagag tcaggaaggg ccacgacaaa | 5201 |
| gcagaaacat cggatttggg gaacgcgtgt catcccttgt gccgcaggct gggcgggaga | 5261 |
| gactgttctg ttctgttcct tgtgtaactg tgttgctgaa agactacctc gttcttgtct | 5321 |
| tgatgtgtca ccggggcaac tgcctggggg cgggatggg ggcagggtgg aagcggctcc | 5381 |
| ccatttttat accaaaggtg ctacatctat gtgatgggtg gggtggggag ggaatcactg | 5441 |
| gtgctataga aattgagatg cccccccagg ccagcaaatg ttcctttttg ttcaaagtct | 5501 |
| atttttattc cttgatattt tttctttctt ttttttttt tttgtggatg gggacttgtg | 5561 |
| aattttctta aaggtgctat ttaacatggg aggagagcgt gtgcgctcca gcccagcccg | 5621 |
| ctgctcactt tccaccctct ctccacctgc ctctggcttc tcaggcctct gctctccgac | 5681 |
| ctctctcctc tgaaaccctc ctccacagct gcagcccatc ctcccggctc cctcctagtc | 5741 |
| tgtcctgcgt cctctgtccc cgggtttcag agacaacttc ccaaagcaca aagcagtttt | 5801 |
| tccctagggg tgggaggaag caaaagactc tgtacctatt tgtatgtgt ataataattt | 5861 |
| gagatgtttt taattatttt gattgctgga ataaagcatg tggaaatgac ccaaacataa | 5921 |

-continued

```
tccgcagtgg cctcctaatt tccttctttg gagttggggg aggggtagac atggggaagg   5981
ggccttgggg tgatgggctt gccttccatt cctgcccttt ccctcccac tattctcttc    6041
tagatccctc cataacccca ctccccttc tctcacccct cttataccgc aaacctttct   6101
acttcctctt tcattttcta ttcttgcaat ttccttgcac cttttccaaa tcctcttctc   6161
ccctgcaata ccatacaggc aatccacgtg cacaacacac acacacactc ttcacatctg   6221
gggttgtcca aacctcatac ccactcccct tcaagcccat ccactctcca cccctggat    6281
gccctgcact tggtggcggt gggatgctca tggatactgg gagggtgagg ggagtggaac   6341
ccgtgaggag gacctggggg cctctccttg aactgacatg aagggtcatc tggcctctgc   6401
tcccttctca cccacgctga cctcctgccg aaggagcaac gcaacaggag agggtctgc    6461
tgagcctggc gagggtctgg gaggaccag gaggaaggcg tgctccctgc tcgctgtcct   6521
ggccctgggg gagtgaggga gacagacacc tgggagagct gtggggaagg cactcgcacc   6581
gtgctcttgg gaaggaagga gacctggccc tgctcaccac ggactgggtg cctcgacctc   6641
ctgaatcccc agaacacaac cccctgggc tggggtggtc tggggaacca tcgtgccccc   6701
gcctcccgcc tactccttt taagctt                                        6728
```

<210> SEQ ID NO 2
<211> LENGTH: 1464
<212> TYPE: PRT
<213> ORGANISM: Homo sapiens

<400> SEQUENCE: 2

```
Met Phe Ser Phe Val Asp Leu Arg Leu Leu Leu Leu Ala Ala Thr
  1               5                  10                  15

Ala Leu Leu Thr His Gly Gln Glu Glu Gly Gln Val Glu Gly Gln Asp
             20                  25                  30

Glu Asp Ile Pro Pro Ile Thr Cys Val Gln Asn Gly Leu Arg Tyr His
         35                  40                  45

Asp Arg Asp Val Trp Lys Pro Glu Pro Cys Arg Ile Cys Val Cys Asp
     50                  55                  60

Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
```

```
              225                 230                 235                 240
Pro Gly Glu Arg Gly Pro Pro Gly Pro Gln Gly Ala Arg Gly Leu Pro
                245                 250                 255
Gly Thr Ala Gly Leu Pro Gly Met Lys Gly His Arg Gly Phe Ser Gly
                260                 265                 270
Leu Asp Gly Ala Lys Gly Asp Ala Gly Pro Ala Gly Pro Lys Gly Glu
                275                 280                 285
Pro Gly Ser Pro Gly Glu Asn Gly Ala Pro Gly Gln Met Gly Pro Arg
                290                 295                 300
Gly Leu Pro Gly Glu Arg Gly Arg Pro Gly Ala Pro Gly Pro Ala Gly
305                 310                 315                 320
Ala Arg Gly Asn Asp Gly Ala Thr Gly Ala Ala Gly Pro Pro Gly Pro
                325                 330                 335
Thr Gly Pro Ala Gly Pro Pro Gly Phe Pro Gly Ala Val Gly Ala Lys
                340                 345                 350
Gly Glu Ala Gly Pro Gln Gly Pro Arg Gly Ser Glu Gly Pro Gln Gly
                355                 360                 365
Val Arg Gly Glu Pro Gly Pro Pro Gly Pro Ala Gly Ala Ala Gly Pro
                370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Pro Pro Gly Pro Lys Gly Asn
                420                 425                 430
Ser Gly Glu Pro Gly Ala Pro Gly Ser Lys Gly Asp Thr Gly Ala Lys
                435                 440                 445
Gly Glu Pro Gly Pro Val Gly Val Gln Gly Pro Pro Gly Pro Ala Gly
                450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
                500                 505                 510
Ser Pro Gly Pro Ala Gly Pro Lys Gly Ser Pro Gly Glu Ala Gly Arg
                515                 520                 525
Pro Gly Glu Ala Gly Leu Pro Gly Ala Lys Gly Leu Thr Gly Ser Pro
                530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
                580                 585                 590
Gly Lys Ala Gly Glu Arg Gly Val Pro Gly Pro Pro Gly Ala Val Gly
                595                 600                 605
Pro Ala Gly Lys Asp Gly Glu Ala Gly Ala Gln Gly Pro Pro Gly Pro
                610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
```

```
Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
            690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
            725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
            755                 760                 765

Ile Gly Pro Pro Gly Pro Ala Gly Ala Pro Gly Asp Lys Gly Glu Ser
            770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
            805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
            850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
            885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
            965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Ala Glu Gly Ser Pro
            1010                1015                1020

Gly Arg Asp Gly Ser Pro Gly Ala Lys Gly Asp Arg Gly Glu Thr Gly
1025                1030                1035                1040

Pro Ala Gly Pro Pro Gly Ala Pro Gly Ala Pro Gly Ala Pro Gly Pro
            1045                1050                1055

Val Gly Pro Ala Gly Lys Ser Gly Asp Arg Gly Glu Thr Gly Pro Ala
            1060                1065                1070
```

Gly Pro Ala Gly Pro Val Gly Pro Val Gly Ala Arg Gly Pro Ala Gly
            1075                1080                1085

Pro Gln Gly Pro Arg Gly Asp Lys Gly Glu Thr Gly Glu Gln Gly Asp
        1090                1095                1100

Arg Gly Ile Lys Gly His Arg Gly Phe Ser Gly Leu Gln Gly Pro Pro
1105                1110                1115                1120

Gly Pro Pro Gly Ser Pro Gly Glu Gln Gly Pro Ser Gly Ala Ser Gly
            1125                1130                1135

Pro Ala Gly Pro Arg Gly Pro Pro Gly Ser Ala Gly Ala Pro Gly Lys
            1140                1145                1150

Asp Gly Leu Asn Gly Leu Pro Gly Pro Ile Gly Pro Pro Gly Pro Arg
            1155                1160                1165

Gly Arg Thr Gly Asp Ala Gly Pro Val Gly Pro Pro Gly Pro Pro Gly
            1170                1175                1180

Pro Pro Gly Pro Pro Gly Pro Pro Ser Ala Gly Phe Asp Phe Ser Phe
1185                1190                1195                1200

Leu Pro Gln Pro Pro Gln Glu Lys Ala His Asp Gly Gly Arg Tyr Tyr
            1205                1210                1215

Arg Ala Asp Asp Ala Asn Val Val Arg Asp Arg Asp Leu Glu Val Asp
            1220                1225                1230

Thr Thr Leu Lys Ser Leu Ser Gln Gln Ile Glu Asn Ile Arg Ser Pro
            1235                1240                1245

Glu Gly Ser Arg Lys Asn Pro Ala Arg Thr Cys Arg Asp Leu Lys Met
1250                1255                1260

Cys His Ser Asp Trp Lys Ser Gly Glu Tyr Trp Ile Asp Pro Asn Gln
1265                1270                1275                1280

Gly Cys Asn Leu Asp Ala Ile Lys Val Phe Cys Asn Met Glu Thr Gly
            1285                1290                1295

Glu Thr Cys Val Tyr Pro Thr Gln Pro Ser Val Ala Gln Lys Asn Trp
            1300                1305                1310

Tyr Ile Ser Lys Asn Pro Lys Asp Lys Arg His Val Trp Phe Gly Glu
            1315                1320                1325

Ser Met Thr Asp Gly Phe Gln Phe Glu Tyr Gly Gly Gln Gly Ser Asp
            1330                1335                1340

Pro Ala Asp Val Ala Ile Gln Leu Thr Phe Leu Arg Leu Met Ser Thr
1345                1350                1355                1360

Glu Ala Ser Gln Asn Ile Thr Tyr His Cys Lys Asn Ser Val Ala Tyr
            1365                1370                1375

Met Asp Gln Gln Thr Gly Asn Leu Lys Lys Ala Leu Leu Leu Lys Gly
            1380                1385                1390

Ser Asn Glu Ile Glu Ile Arg Ala Glu Gly Asn Ser Arg Phe Thr Tyr
            1395                1400                1405

Ser Val Thr Val Asp Gly Cys Thr Ser His Thr Gly Ala Trp Gly Lys
            1410                1415                1420

Thr Val Ile Glu Tyr Lys Thr Thr Lys Ser Ser Arg Leu Pro Ile Ile
1425                1430                1435                1440

Asp Val Ala Pro Leu Asp Val Gly Ala Pro Asp Gln Glu Phe Gly Phe
            1445                1450                1455

Asp Val Gly Pro Val Cys Phe Leu
            1460

<210> SEQ ID NO 3
<211> LENGTH: 20
<212> TYPE: DNA

```
<213> ORGANISM: Homo sapiens
<220> FEATURE:
<223> OTHER INFORMATION: Antisense oligonucleotide

<400> SEQUENCE: 3
ggacgaccag gttttccagc                                               20

<210> SEQ ID NO 4
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 4
gcagcaccag cagggccagg                                               20

<210> SEQ ID NO 5
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 5
gccaggagca ccaggttcac                                               20

<210> SEQ ID NO 6
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 6
cttcctctcc agcagggcca                                               20

<210> SEQ ID NO 7
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 7
gccttgccgg gctctccagc                                               20

<210> SEQ ID NO 8
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 8
cgggaacacc tcgctctcca                                               20

<210> SEQ ID NO 9
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 9
gcaggaccga cagcgccagg                                               20
```

```
<210> SEQ ID NO 10
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 10
tccatctttg ccagcaggac                                               20

<210> SEQ ID NO 11
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 11
ggtccctgag ctccagcctc                                               20

<210> SEQ ID NO 12
<211> LENGTH: 19
<212> TYPE: DNA
<213> ORGANISM: Homo sapiens
<220> FEATURE:
<223> OTHER INFORMATION: Antisense oligonucleotide

<400> SEQUENCE: 12
ttggccgtca gcaccaggg                                                19

<210> SEQ ID NO 13
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 13
tttctcgcca gcagggccag                                               20

<210> SEQ ID NO 14
<211> LENGTH: 20
<212> TYPE: DNA
<213> ORGANISM: Homo sapiens
<220> FEATURE:
<223> OTHER INFORMATION: Antisense oligonucleotide

<400> SEQUENCE: 14
ctcgatctgc tggctcaggc                                               20
```

ANTISENSE OLIGONUCLEOTIDES TO TYPE I PROCOLLAGEN

The present invention relates to antisense oligonucleotides and their use in inhibiting expression of type I procollagen.

The collagens are a family of closely related proteins, with a triple helix protein structure. Numerous collagen types have been identified (>10) of which type I procollagen (consisting of two alpha1 chains and one alpha2 chain) is the principal component of bone, skin, and tendon.

It has been recognised for many years that many pathological conditions are caused by overproduction of collagen fibres in the form of scars and excess fibrous tissues. For example, liver cirrhosis is a two-step process in which normal liver tissue is first destroyed by a virus or by alcohol and other toxins, and then excessive amounts of collagen fibres replace the damaged cells before normal liver cell regeneration. Idiopathic pulmonary fibrosis is a lethal condition in which normal lung tissue is gradually replaced by excessive amounts of collagen fibres. Progressive systemic sclerosis (scleroderma) is a frequently lethal disease where skin and many internal organs become leather-like because of excessive depositions of collagen fibres. In many individuals, wounds or surgical incisions in the skin are followed by excessive depositions of collagen in the form of hypertrophic scars and keloids that present cosmetic problems and sometimes more serious consequences. Also, excessive scarring frequently occurs in normal individuals following trauma and surgical procedures. In these and related conditions, a means of specifically inhibiting collagen synthesis and deposition would be of tremendous benefit.

PCT Patent Application Publication No. WO 94/11494 discloses a DNA or RNA oligonucleotide comprising from 5 to 200 nucleotides substantially complementary to a mutant collagen nucleotide sequence or a normal wild type collagen nucleotide sequence which is capable of inhibiting collagen gene expression. Preferred oligonucleotides are said to be antisense oligonucleotides. The Examples of WO 94/11494 describe a series of DNA oligonucleotides, some of which are antisense, that were synthesised primarily with regard to the region at the 3' end of exon 1 (from nucleotides 198 to 222) and the first two nucleotides of intron 1 of the human gene for the proα1 chains of type I procollagen (COL1A1). The synthesised oligonucleotides were found to vary considerably in their ability to inhibit expression of an internally deleted mutant COL1A1 gene of human origin. The effectiveness of the oligonucleotides in inhibiting the expression of the human wild type COL1A1 gene was not however demonstrated. Since the structure and conformation of the RNA transcripts of the human, mutant and wild type COL1A1 genes would most likely differ, it would not necessarily follow that oligonucleotides which are effective inhibitors of the expression of the mutant COL1A1 gene would also be effective inhibitors of the expression of the wild type COL1A1 gene.

It would be desirable to identify antisense DNA oligonucleotides that are capable of inhibiting the expression of a wild type COL1A1 gene.

In accordance with the present invention, there is therefore provided an antisense DNA oligonucleotide comprising from 18 to 25 nucleotides which is complementary to a nucleotide sequence from position 750 to position 3900 inclusive of SEQ ID NO:1, wherein SEQ ID NO:1 comprises a nucleotide sequence encoding a polypeptide comprising an amino acid sequence according to SEQ ID NO:2, the oligonucleotide being capable of inhibiting expression of the polypeptide in a cell that expresses it.

SEQ ID NO:1 is identical to the nucleotide sequence registered under EMBL accession no. Z74615. SEQ ID NO:2 is the amino acid sequence of the polypeptide encoded by the nucleotide sequence of SEQ ID NO:1. The polypeptide encoded by SEQ ID NO:1 is a precursor of the wild type, proα1 chain of type I procollagen ("prepro-alpha1 (I) collagen").

The antisense DNA oligonucleotide according to the invention comprises 18, 19, 20, 21, 22, 23, 24 or 25 nucleotides and is preferably 20 nucleotides in length.

The antisense DNA oligonucleotide is preferably complementary to a nucleotide sequence in one of the following regions of SEQ ID NO:1,

| | |
|---|---|
| Region 1 | from position 750 to position 900 inclusive, |
| Region 2 | from position 1200 to position 1300 inclusive, |
| Region 3 | from position 1400 to position 1500 inclusive, |
| Region 4 | from position 1450 to position 1550 inclusive, |
| Region 5 | from position 1850 to position 2000 inclusive, |
| Region 6 | from position 2500 to position 2600 inclusive, |
| Region 7 | from position 2850 to position 2950 inclusive, |
| Region 8 | from position 3800 to position 3900 inclusive. |

Particularly preferred antisense DNA oligonucleotides are those which are complementary to a nucleotide sequence in Region 2, 4, 6 or 8 of SEQ ID NO:1.

The oligonucleotides of the invention may be prepared by any suitable method known in the art. The oligonucleotides are very conveniently prepared by synthetic chemical methods, for example, phosphoramidite chemistry by sulfurization with tetraethylthiuram disulfide in acetonitrile as described in *Tetrahedron Lett.*, 1991, 32, 30005–30008.

The oligonucleotides of the present invention are advantageous in that they inhibit expression of the wild type COL1A1 gene. They are therefore useful in the treatment or prevention of conditions/disorders caused by overproduction of collagen fibres, for example, liver cirrhosis, kidney, liver and heart fibrosis, scleroderma, hypertrophic scars and keloids.

Accordingly, the present invention provides an antisense DNA oligonucleotide according to the invention for use in therapy.

In another aspect, the invention provides the use of an antisense DNA oligonucleotide according to the invention in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of treating, or reducing the risk of, a collagen disorder in a patient suffering from, or at risk of, the disorder, which comprises administering to the patient a therapeutically effective amount of an antisense DNA oligonucleotide according to the invention.

For the above-mentioned therapeutic uses the dosage administered will, of course, vary with the oligonucleotide employed, the mode of administration, the treatment desired and the disorder indicated. Effective dosages are those which are able to inhibit collagen protein production in cells at a level which eliminates or reduces the symptoms or conditions associated with the collagen protein production.

The oligonucleotides according to the invention will generally be administered in the form of a pharmaceutical composition in which the oligonucleotide is formulated with a pharmaceutically acceptable adjuvant, diluent or carrier.

Thus, the present invention also provides a pharmaceutical composition comprising an antisense DNA oligonucleotide according to the invention in association with a pharmaceutically acceptable adjuvant, diluent or carrier.

The invention further provides a process for the preparation of a pharmaceutical composition of the invention which comprises mixing the antisense DNA oligonucleotide with a pharmaceutically acceptable adjuvant, diluent or carrier.

The pharmaceutical composition of the invention may be administered topically in the form of, for example, a creme, lotion or ointment; or systemically, e.g. by oral administration in the form of tablets, capsules, syrups, powders or granules, or by parenteral administration in the form of sterile solutions or suspensions.

The present invention will now be further explained by reference to the following illustrative Examples.

EXAMPLES

Example 1

Oligonucleotide Synthesis

Phosphorothioate oligodeoxynucleotides synthesis was carried out at a 1 μm scale on PE Biosystems 394 DNA synthesizer using phosphoramidite chemistry with TETD/acetonitrile sulphurizing reagent. Oligonucleotides were purified on Poly-Pak TM II cartridges (Glen Research), desalted on NAPTM 10 columns (Amersham Pharmacia Biotech AB) and ion-exchanged using Dowex 50WX8-1100 ion exchange resin (Aldrich). Twelve antisense DNA oligonucleotides (ASOs) were prepared having the following sequences (5'→3'):

| 1.  | GGACGACCAGGTTTTCCAGC | (SEQ ID NO:3)  |
| --- | --- | --- |
| 2.  | GCAGCACCAGCAGGGCCAGG | (SEQ ID NO:4)  |
| 3.  | GCCAGGAGCACCAGGTTCAC | (SEQ ID NO:5)  |
| 4.  | CTTCCTCTCCAGCAGGGCCA | (SEQ ID NO:6)  |
| 5.  | GCCTTGCCGGGCTCTCCAGC | (SEQ ID NO:7)  |
| 6.  | CGGGAACACCTCGCTCTCCA | (SEQ ID NO:8)  |
| 7.  | GCAGGACCGACAGCGCCAGG | (SEQ ID NO:9)  |
| 8.  | TCCATCTTTGCCAGCAGGAC | (SEQ ID NO:10) |
| 9.  | GGTCCCTGAGCTCCAGCCTC | (SEQ ID NO:11) |
| 10. | TTGGCCGTCAGCACCAGGG  | (SEQ ID NO:12) |
| 11. | TTTCTCGCCAGCAGGGCCAG | (SEQ ID NO:13) |
| 12. | CTCGATCTGCTGGCTCAGGC | (SEQ ID NO:14) |

Example 2

Treatment of Cells

The human cell line WI-26 was grown in Dulbecco's modified Eagle's medium (DMEM) containing 10% fetal calf serum. The cells were plated in 48-well plates or 6-well plates (Costar, Corning Inc.) to obtain 70–80% confluence. After 24 hours, the cells were washed two times with pre-warmed DMEM and 0.35 ml (for 48-well experiments) or 1 ml (6-well experiments) DMEM containing 5 μg/ml lipofectin (Gibco BRL) or 2.5 μg/ml cytofectin GSV (Glen Research Ltd) and oligonucleotides at 200 nM were added to each well. After 4–5 hours at 37° C. the cells were washed two times with pre-warmed DMEM and 0.35 ml DMEM (48-well plates) or 1 ml DMEM (6-well plates) was added together with ascorbic acid at 20 ug/ml. The cells were incubated for 20 hours prior to analysis of collagen levels.

Example 3

Protein Analysis

At the end of the experiment, 150 μl of medium was removed and the amount of secreted type I procollagen determined using an ELISA kit (AmershamPharmacia Ltd) and the results expressed as nanograms of procollagen in the medium/10,000 cells. To correct for cell numbers, plates were washed with pre-warmed PBS, cells treated with trypsin and cell numbers determined using an automated Coulter counter. For 6-well experiments, the cells were counted, treated with 1 ml TRI reagent (SIGMA Ltd) and proteins and RNA extracted according to the manufacturers guidelines. The protein pellet was re-suspended in 1% SDS containing protease inhibitors. 30–100 ugs cellular proteins were heated at 100° C. for 5 mins and then lectrophoresed in a 4–12% SDS polyacrylamide gel. Proteins were electrophoretically transferred to nitrocellulose filters and hybridised with an antibody against a synthetic peptide corresponding to human proα1 (I) chain of type 1 collagen (obtained from Dr Larry Fisher, NIH, USA). The proα1 (1) band was detected using an anti-rabbit secondary antibody coupled to HRP (Biorad Ltd) and developed using ECL (Pierce Ltd). Protein loading was determined by treating the membrane with an antibody to GAPDH (Advanced Immunochemicals). Protein loading was normalised to GAPDH levels using desitometry.

Example 4

RNA Analysis

RNA was extracted using TRI reagent and the final pellet was re-suspended in 0.5% SDS. One to three micrograms of total RNA were electrophoresed in a formaldehyde denaturing gel according to standard procedures (Sambrook, J., Fritsch, E. F. and Maniatis, T. (1989) Molecular Cloning: A Laboratory Manual, 2nd Ed., Cold Spring Harbor Laboratory Press, Cold Spring Harbor, N.Y.). RNA was transferred to Hybond-N membranes (Amersham) and hybridised for 24 hours to an alpha1 (1) cDNA probe radiolabeled using a T7 polymerase kit (AmershamPharmacia). Following washing, the filter was exposed to X-ray film and the film developed 4–24 hours later. The autoradiographic images of the alpha1 (1) transcripts (4.8 kb & 5.8 kb) were analysed by densitometric analysis and RNA loading was corrected using the intensity of the GAPDH transcript or the intensity of the 28S rRNA as internal controls.

Results

Table I below shows the average percentage (%) collagen inhibition which relates to either collagen levels in the medium or collagen mRNA levels. In the treated cell assay used, there was a very good correlation between percentage collagen inhibition as measured in the medium and percentage inhibition of intracellular collagen mRNA levels.

TABLE I

| ASO | AVERAGE % COLLAGEN INHIBITION |
|---|---|
| GGACGACCAGGTTTTCCAGC (SEQ ID NO:3) | 50 |
| GCAGCACCAGCAGGGCCAGG (SEQ ID NO:4) | 50–80 |
| GCCAGGAGCACCAGGTTCAC (SEQ ID NO:5) | 50 |
| CTTCCTCTCCAGCAGGGCCA (SEQ ID NO:6) | 50–60 |
| GCCTTGCCGGGCTCTCCAGC (SEQ ID NO:7) | 50 |
| CGGGAACACCTCGCTCTCCA (SEQ ID NO:8) | 50 |

TABLE I-continued

| ASO | AVERAGE % COLLAGEN INHIBITION |
|---|---|
| GCAGGACCGACAGCGCCAGG (SEQ ID NO:9) | 50 |
| TCCATCTTTGCCAGCAGGAC (SEQ ID NO:10) | 50 |
| GGTCCCTGAGCTCCAGCCTC (SEQ ID NO:11) | 50 |
| TTGGCCGTCAGCACCAGGG (SEQ ID NO:12) | 50–80 |
| TTTCTCGCCAGCAGGGCCAG (SEQ ID NO:13) | 50–70 |
| CTCGATCTGCTGGCTCAGGC (SEQ ID NO:14) | 50–80 |

The invention claimed is:

1. An antisense DNA oligonucleotide comprising 20–25 nucleotides which is complementary to SEQ ID NO: 1, wherein SEQ ID NO: 1 comprises a nucleotide sequence encoding a polypeptide comprising an amino acid sequence according to SEQ ID NO: 2, the oligonucleotide being capable of inhibiting expression of the polypeptide in a cell that expresses it, in which said oligonucleotide is SEQ ID NO: 14.

2. A composition comprising an oligonucleotide as defined in claim 1 in association with a pharmaceutically acceptable adjuvant, diluent, or carrier.

* * * * *